(12) United States Patent
Mayer et al.

(10) Patent No.: US 8,613,859 B2
(45) Date of Patent: *Dec. 24, 2013

(54) SYNERGISTIC BIOCIDE AND PROCESS FOR CONTROLLING GROWTH OF MICROOGANISMS

(75) Inventors: Michael J. Mayer, Jacksonville, FL (US); Freddie L. Singleton, Vernon Hills, IL (US)

(73) Assignee: Hercules Incorporated, Wilmington, DE (US)

( * ) Notice: Subject to any disclaimer, the term of this patent is extended or adjusted under 35 U.S.C. 154(b) by 280 days.

This patent is subject to a terminal disclaimer.

(21) Appl. No.: 12/911,463

(22) Filed: Oct. 25, 2010
(Under 37 CFR 1.47)

(65) Prior Publication Data
US 2011/0159117 A1    Jun. 30, 2011

Related U.S. Application Data

(63) Continuation-in-part of application No. 11/509,158, filed on Aug. 24, 2006, now Pat. No. 7,820,060.

(60) Provisional application No. 60/711,508, filed on Aug. 26, 2005.

(51) Int. Cl.
*C02F 1/76* (2006.01)
*C02F 1/50* (2006.01)

(52) U.S. Cl.
USPC ........... 210/754; 210/755; 210/756; 210/759; 210/760; 210/764; 424/661; 424/664; 422/37; 162/161

(58) Field of Classification Search
USPC ................ 210/754, 755, 756, 759, 760, 764; 422/37; 424/661, 664; 162/161
See application file for complete search history.

(56) References Cited

U.S. PATENT DOCUMENTS 7,820,060 B2 * 10/2010 Mayer et al. ................... 210/754
2005/0211643 A1 * 9/2005 Phillips et al. ................ 210/753

* cited by examiner

*Primary Examiner* — Ana M Fortuna
*Assistant Examiner* — Nader Hossaini
(74) *Attorney, Agent, or Firm* — Joanne Rossi; Shaorong Chen; Michael Herman

(57) ABSTRACT

Synergistic mixtures of haloamines and their use to control the growth of microorganisms in aqueous systems are disclosed. The method of using the synergistic mixtures entails adding an effective amount of a monohaloamine and an effective amount of a dihaloamine to an aqueous system. The ratio of monohaloamine to dihaloamine is selected to result in a synergistic biocidal effect.

19 Claims, No Drawings

SYNERGISTIC BIOCIDE AND PROCESS FOR CONTROLLING GROWTH OF MICROOGANISMS

This application claims priority on and is a continuation in part of U.S. Ser. No. 11/509,158, now U.S. Pat. No. 7,820,060, filed Aug. 24, 2006 which claims the benefit of U.S. Provisional Application No. 60/711,508 filed Aug. 26, 2005, the entire contents of U.S. Ser. No. 11/509,158, now U.S. Pat. No. 7,820,060, and U.S. 60/711,508 are herein incorporated by reference.

FIELD OF THE INVENTION

The present invention relates to synergistic mixtures (or combinations) of haloamines and their use to control the growth of microorganisms in aqueous systems, more particularly in industrial process waters.

BACKGROUND OF THE INVENTION

Uncontrolled growth of microorganisms in industrial production systems can have serious consequences such as lowered product quality, degradation or spoilage of products, contamination of products, and interference with a wide range of important industrial processes. Growth of microorganisms on surfaces exposed to water (e.g., recirculation systems, heat exchangers, once-through heating and cooling systems, pulp and paper process systems, etc.) can be especially problematic, as many of these systems provide an environment suitable for growth of bacteria and other types of microorganisms. Industrial process waters often provide conditions of temperature, nutrients, pH, etc. that allow for abundant growth of microorganisms. Uncontrolled growth of microorganisms is often manifested in the water column with large numbers of free-floating (planktonic) cells as well as on submerged surfaces where conditions favor formation of biofilms.

The process leading to the formation of biofilms is described in detail as follows. The first stage of biofilm formation is for planktonic cells to contact submerged surfaces either as a result of turbulence in water flow or by active movement toward the surface. If the physical and chemical characteristics of surface, including the surface-water interface, are favorable for growth, microorganisms can attach to the surface, grow, and begin to produce exopolysaccharides that provide three-dimensional integrity to the biofilm. Over time, the biofilm becomes thicker and internally complex as cells reproduce and produce more exopolysaccharides. The microbial community of a biofilm can consist of single or multiple species.

Biofilms are seemingly ubiquitous in all natural, medical, and industrial settings where bacteria exist. Microorganisms can form biofilms on a wide variety of abiotic hydrophobic and hydrophilic surfaces, including glass, metals, and plastics.

Many types of processes, systems, and products can be adversely affected by uncontrolled growth of microorganisms in biofilms and in industrial process waters. Such problems include accelerated corrosion of metals, accelerated decomposition of wood and other biodegradable materials, restricted flow through pipes, plugging or fouling of valves and flow-meters, and reduced heat exchange or cooling efficiency on heat exchange surfaces. Biofilms may also be problematic relative to cleanliness and sanitation in medical equipment, breweries, wineries, dairies and other industrial food and beverage process water systems. Moreover, sulfate-reducing bacteria are often problematic in waters used for the secondary recovery of petroleum or for oil drilling in general. Although sulfate-reducing bacteria can form biofilms on equipment and in pipelines, the significant problem caused by these bacteria is that they generate metabolic by-products that have highly offensive odors, are toxic, and can cause corrosion of metal surfaces by accelerating galvanic action. For example, these microorganisms reduce sulfates present in the injection water to generate hydrogen sulfide, a highly toxic gas that has a highly offensive odor (i.e., rotten egg odor), is corrosive, and reacts with metal surfaces to form insoluble iron sulfide corrosion products.

Paper production is particularly susceptible to adverse effects of biofilms. Paper process waters have conditions (e.g., temperature and nutrients) that favor growth of microorganisms in the water and on exposed surfaces. Biofilms on surfaces in paper process systems can be very thick and contain paper fiber and other materials used in paper production; such resulting material is referred to as slime or a slime deposit. Slime deposits can become dislodged from system surfaces and become incorporated into the paper, which results in increased breaks and tears in the sheet. Furthermore, slime can cause unsightly blemishes or holes in the final product, which result in a lower quality product or the product being rejected. This necessitates stopping paper production to clean the equipment, which results in the loss of production time.

In order to control problems caused by microorganisms in industrial process waters, numerous antimicrobial agents (i.e., biocides) have been employed to eliminate, to inhibit or to reduce microbial growth. Biocides are used alone or in combination to prevent or control the problems caused by growth of microorganisms. Biocides are usually added directly to a process water stream or to a material used in the process. When used to prevent biofilm formation, the typical method of addition is such that the biocide is distributed throughout the process system. In this manner, planktonic microorganisms and those in biofilms on surfaces in contact with the process water can be controlled.

Many organic and inorganic substances are used as biocides in industrial process systems. The type of biocide used in a given system will depend on many factors including, but not limited to, the nature of the medium to which the biocide is added, the problematic microorganism(s), as well as specific requirements of the industry, including safety and regulatory considerations. Not all biocides are interchangeable. A biocide that works well on one environment may not work in another environment. For instance, biofilm forming organisms are difficult to control because many biocides can not penetrate the sheath formed around the organism.

Depending on their chemical composition and mode-of-action, biocides are classified as oxidizing or non-oxidizing. Oxidizing and non-oxidizing biocide can be used alone or in combination depending on the application. Oxidizing biocides have been widely used in industry for decades, especially in pulp and paper production where strong oxidizers have been used to control microbial populations. Oxidizing biocides such as chlorine gas, sodium hypochlorite, hypobromous acid, and chlorine dioxide are widely used as biocides to treat recirculating waters in many types of industries. Two of the primary reasons for using these and other oxidizing biocides is that such oxidizers are: (1) inexpensive; and (2) non-specific regarding which types of microorganisms are inhibited; if sufficient concentrations of oxidizing biocides are achieved virtually all microorganisms can be inhibited.

Of the oxidizing biocides, chlorine is the most widely used to treat recirculating water systems. The chemistry of chlorine is well known. Other halogens such as Bromine, Fluorine, and Iodine are known to have antimicrobial activity. When added to water, chloride can exist in either of two forms, HOCl and OCl⁻, depending on pH. Bromine reacts with water similar to chlorine. These chemical species of chlorine, also referred to as "free chlorine," react with a wide variety of compounds in aqueous systems.

HOCl (hypochlorous acid) is much more effective as a disinfectant than OCl⁻ (hypochlorite). When HOCl contacts a microorganism, the oxidizer can rapidly interact with any of a number of cellular constituents resulting in inhibition of growth. It has been reported that a very short contact time (i.e., <0.1 sec) is required to inhibit a cell. Chlorine contacting a microorganism may rapidly cause a Fenton-type reaction in which hydroxyl radicals are generated and those radicals are responsible inhibitory effects.

The highly reactive nature of chlorine may also be a liability, as some of the oxidizer will be used (e.g., consumed) during reactions with non-biological material. Therefore, in order to provide enough oxidizer to react with microorganisms in a process stream, the total amount of oxidizer needed to inhibit microorganisms will include that used in reactions with non-biological components of the system. Reactions with non-biological components of process water not only add to treatment cost, but undesired by-products can be generated and other additives in the process stream can be adversely affected.

Process streams such as in paper mills are especially problematic for highly reactive oxidizers because of the high concentrations of dissolved and particulate inorganic and organic materials. Such process waters exhibit a very high "demand" on the oxidizer. "Demand" is defined as the amount of chlorine that reacts with substances other than the target microorganisms in the process water. In order to maintain an effective concentration of chlorine in an aqueous system to inhibit microorganisms, an amount in excess of the demand must be applied. The types and amounts of inorganic and organic materials in a process stream will define the demand for an oxidizer. For example, many substances are known to react with chlorine and result in the chlorine being non-biocidal; such substances include sulfides, cyanides, metal ions, lignin, and, among others, various water treatment chemicals (e.g., some scale and corrosion inhibitors).

Although effective as biocides, strong oxidizers such as sodium hypochlorite can cause many problems in an industrial process stream such as increased corrosion rates, increased consumption of wet end additives, and, among others, decreased life of felts used on papermachines.

Because of the inherent reactivity of chlorine and related strong oxidizers with non-biological organic and inorganic materials, it is desirable to have the oxidizer in a form that would have antimicrobial activity but be less reactive with non-biological materials. The process of chloramination has been used to avoid some of the problems associated with the use of strong oxidizers. Chloramination can occur in a number of ways (1) adding chlorine to a water system that contains a known, low concentration of ammonia, or (2) adding ammonia to a water system that contains a known, low concentration of chlorine. In either situation, the chlorine and ammonia react in situ to form a chloramine. Chloramines generated from reacting chlorine and ammonia includes monochloramine ($NH_2Cl$), dichloramine ($NHCl_2$), and trichloramine ($NCl_3$). Two of the important parameters that determine which chloramine species will exist in a system are pH and the ratio of Cl to N.

Chlorine, as a gas or liquid, and ammonia are commonly combined to form chloramines. Other halogens such as bromine can be substituted for chlorine. Other substances containing an amine ($RNH_2$) group can also form haloamines, such as chloramines. The antimicrobial activity of a chloramine depends on the chemical nature of the amine-containing compound. For example, ammonium hydroxide can react with an oxidizing halogen donor such as sodium hypochlorite to form monochloramine; this chloramine will be an effective biocide. However, if an amino acid, such as glycine ($NH_2CH_2CO_2H$) is reacted with sodium hypochlorite, the amine group will be chlorinated, forming a mono- or di-chloramine species. The chlorinated glycine has less antimicrobial activity compared to monochloramine generated from ammonium hydroxide.

Chloramines are attractive for water treatment because of their stability in situ, ease of application and monitoring, and low capital and operational costs. Although laboratory studies have demonstrated that free chlorine is more effective than chloramines at inactivating microorganisms, studies have also documented that the antimicrobial activity of chloramines is greater at lower pH as well as higher temperatures and concentrations.

Methods for production of chloramines in highly concentrated form, including anhydrous chloramine, have been patented (U.S. Pat. Nos. 2,678,258; 2,837,409; 3,038,785; 2,710,248; and 3,488,164, the contents of each is herein incorporated by reference).

Monochloramine is the preferred chemical species for disinfecting a water supply. Dichloramine is reported to be a superior disinfectant but has negative properties such has high volatility and odor. The difference in reactivity and specificity of chlorine and monochloramine may allow the latter to penetrate a biofilm and react with the denizens whereas the former is consumed in non-specific reactions with materials in the water or abiotic components of the biofilm before it fully penetrates the biofilm.

Monochloramine is used as a single active to treat water for controlling growth of microorganisms in water and wastewater systems. Studies have shown that the pH of an aqueous system affects efficacy of monochloramine; the efficacy increases as pH decreases. Other physical and chemical parameters of a system can affect efficacy of chloramines by influencing the stability of the compounds. For example, it has been demonstrated that parameters such as pH, temperature, and the presence of other chemicals have influence on the stability of monochloramine in water, monochloramine has a significantly longer stability at 4° C. than it does at 35° C.

Although widely practiced for treating municipal water distribution systems, chloramines are not commonly used in industrial systems. Chlorine (in bleach or chlorine gas) was used in combination with ammonia in papermaking systems. There was a shift toward using other oxidizing and non-oxidizing biocides in papermaking systems in subsequent years. However, recently there appears to be renewed interest in using chloramines in papermaking systems (see U.S. Pat. Nos. 6,478,973; 6,132,628; 5,976,386, the contents of each is herein incorporated by reference). For example, it has been shown that ammonium bromide activated with sodium hypochlorite produces an effective biocide for industrial applications. Furthermore, this biocide is especially effective for controlling problems associated with microbial growth in pulp and paper process waters that have a pH in the alkaline range. The biocide generated from ammonium bromide, described as a "bromide-activated chloramine," effectively reduces the total microbial community within a system (i.e., biofilm-associated as well as planktonic bacteria) where the pH is neutral to alkaline. The preferred pH of the receiving water should be in the range of 7 to 9; the biocide is effective in alkaline paper process water but does not interfere with other pulp and paper process and functional additives (e.g., wet and dry strength additives, size agents, dyes, etc), unlike other common oxidizer programs.

There remains a need for improved biocides that are effective under harsh environmental conditions such as found in the papermaking industry and other industrial processes.

SUMMARY OF THE INVENTION

The present invention relates to the use of certain mixtures (or combinations) of haloamines and processes or methods to prevent the growth of microorganisms in industrial process waters.

More specifically the present invention is directed to the use of synergistic mixtures (or combinations) containing monohaloamine and dihaloamine, examples of such are monochloramine and dichloramine. In the invention microbial populations in aqueous industrial process waters are controlled by administering effective amounts of monohaloamine and dihaloamine to aqueous systems, the result is synergistic.

The novel mixtures (or combinations) of haloamines and processes (methods) incorporating the composition of the present invention show unexpected synergistic activity against microorganisms.

DETAILED DESCRIPTION OF THE INVENTION

For the purposes of this invention, haloamines are defined as chemicals with a composition that includes one or more halogen atoms associated with an amine group and possess antimicrobial activity. The nitrogen may or may not be bonded to another atom other than hydrogen. Halogen atoms include chlorine, fluorine, bromine, and iodine. Chlorine is the most preferred halogen used in the present invention.

The present invention is directed to novel synergistic biocidal mixtures (or combinations) comprising monohaloamine and dihaloamine such as monochloramine and dichloramine, in an aqueous system. These novel synergistic biocidal mixtures (or combinations) when used in combination in an aqueous system are effective in inhibiting or controlling the growth of microorganisms in the aqueous system. The present invention is also directed to a method of inhibiting or controlling the growth of microorganisms by administering or adding an effective amount of monohaloamine and an effective amount of dihaloamine, to result in a synergy index of less than 1 as defined herein. The preferred haloamines are chloramines and bromamine.

Monohaloamine, when used with dihaloamine in aqueous systems, unexpectedly provided enhanced biocidal activity, which is greater than that of the individual components. The microbiocidal mixtures (or combinations) of the present invention possess a high degree of antimicrobial activity which could not have been predicted from the known activities of the individual ingredients comprising the combinations. The enhanced activity of the mixtures (or combinations) permits a significant reduction in the total quantity of the biocide required for an effective treatment of an aqueous system.

The aqueous systems to be treated have pH values of between 4 and 10, preferable between 5 and 9 and more preferably between 5 and 8.

Monohaloamine, when used with dihaloamine in aqueous systems, unexpectedly provided enhanced biocidal activity, which is greater than that of the individual components.

Examples of monohaloamines and dihaloamines include chloramines, bromamines, and iodoamines. The microbiocidal mixtures (or combinations) of the present invention possess a high degree of antimicrobial activity which could not have been predicted from the known activities of the individual ingredients comprising the combinations. The enhanced activity of the mixtures (or combinations) permit a significant reduction in the total quantity of the biocide required for an effective treatment of an aqueous system.

Because of the inherent reactivity of halogens, for example chlorine, and related strong oxidizers with non-biological organic and inorganic materials, it is desirable to have the oxidizer in a form that would have antimicrobial activity but be less reactive with non-biological materials. The process of chloramination has been used to avoid some of the problems associated with the use of strong oxidizers. The process of chloramination can generate chloramines including monochloramine ($NH_2Cl$), dichloramine ($NHCl_2$), and trichloramine ($NCl_3$). Two of the important parameters that determine which chloramine species will exist in a system are pH and the ratio of Cl to N. As the pH of the aqueous system is decreased the monohaloamine species will convert to a dihaloamine species. As the amount of chlorine in the system increases with respect to the amount of available amine source the equilibrium pushes the monohaloamine species to a dihaloamine species.

Chlorine, as a gas or liquid, and ammonia are commonly combined to form chloramines. However, other substances containing an amine group can also form chloramines or haloamines. The antimicrobial activity of a haloamine such as chloramine depends on the chemical nature of the amine-containing compound. For example, ammonium hydroxide can react with an oxidizing halogen donor such as sodium hypochlorite to form monochloramine; this chloramine will be an effective biocide. However, if an amino acid, such as glycine ($NH_2CH_2CO_2H$) is reacted with sodium hypochlorite, the amine group will be chlorinated, forming a mono- or di-chloramine species. The chlorinated glycine has less antimicrobial activity compared to monochloramine generated from ammonium hydroxide.

The present invention is relates to synergistic mixtures (or combination) containing monohaloamine and dihaloamine. Haloamines, both monohaloamine and dihaloamine, can be produced by combining an amine source or ammonium source with a halogenated oxidant. An amine source or ammonium source can be combined with a non halogenated oxidant to form a haloamine if the system also contains a halogen source. Examples of halogen sources include but are not limited to, a halogen containing salt or acid. Examples of haloamines are chloramines (monochloramine or dichloramine) and bromamines (monobromamine and dibromamine). The haloamine mixture can be adjusted to obtain the desired ratio of monohaloamine to dihaloamine by adjusting the pH and/or the halogen to nitrogen ratio. Once monochloramine is converted to dichloramine it is stable and does not readily convert back.

Dichloramine can be produced from a monochloramine solution. One method of producing dichloramine from monochloramine is to reduce the pH of the monochloramine solution. Another method of producing a dichloramine from a monochloramine solution is to adjust the chlorine to nitrogen ratio in the solution, for example by adding additional chlorine to the monochloramine solution. Once monochloramine is converted to dichloramine it is stable and does not readily convert back. The pH and the Cl to N ratios can be balanced to produce the desired blend of mono and dichloramines. Monobromamine readily converts to dibromamine at pH's below 12. Under most conditions, at pH of 10 or less, bromamine will exist as dibromamine.

Any method that can be used to produce a haloamine is contemplated as a possible source of haloamine for the purposes of this invention. The ratio of monohaloamine to dihaloamine can be adjusted by known methods to achieve the desire ratio that produces a synergistic biocidal effect.

In one variation of the invention, an amine or ammonium source is reacted with a halogen containing oxidant to produce monohaloamine. The pH of the monohaloamine is then adjusted to achieve the desired ratio of mono to di haloamines.

In another variation, an amine or ammonium source is reacted with a halogen containing oxidant to produce monohaloamine. The chlorine to nitrogen ratio of the monohaloamine is then adjusted to achieve the desired ratio of mono to di haloamines.

In a third variation, an amine or ammonium source is reacted with a halogen containing oxidant to produce monohaloamine. A portion of the monohaloamine is then separated and adjusted to produce dihaloamine. The dihaloamine and the monohaloamine are used in a ratio in the system to be treated to achieve the desired ratio of mono to di haloamines.

In a fourth variation, the monohaloamine and the dihaloamine are produced separately and contacted with the aqueous system to be treated separately or in a common conduit. The amounts of mono and di chloramines are selected to achieve the desired ratio of mono to di haloamines to produce the synergistic effect.

The amine sources or ammonium sources used in the present invention include, but are not limited to, ammonia and ammonium salts and amines. What is meant by ammonium salts are those salts that have a $NH_4^+$ cation and a related anion. Examples of ammonium salts include, but are not limited to, ammonium acetate, ammonium bicarbonate, ammonium bifluoride, ammonium bromide, ammonium carbonate, ammonium chloride, ammonium citrate, ammonium fluoride, ammonium hydroxide, ammonium iodide, ammonium molybdate ammonium nitrate, ammonium oxalate, ammonium persulfate, ammonium phosphate, ammonium sulfate, ammonium sulfide, ferric ammonium sulfate, ferrous ammonium sulfate and ammonium sulfamate. Preferred ammonium salts are ammonium carbonate, ammonium citrate, ammonium hydroxide, ammonium sulfate and ammonium chloride. Quaternary ammonium salts are not considered amine sources for the present invention and are not included in the term ammonium salts for the purposes of this invention.

The amine sources useful in the present invention can also be primary amines ($RNH_2$) or secondary amities ($R_2NH$). Additional ammonium and/or amine sources included ammonia, dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallow-methylamine, cocomethylamine, n-alkylamines, n-acetylglucosamine, diphenylamine, ethanol/methylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, polyamines, primary amines, secondary amines, cyclic amines, bicyclic amines, oligocyclic amines, aliphatic amines, aromatic amines, primary and secondary nitrogen containing polymers. Quaternary amines are not included in the amine source useful in this invention. Quaternary amines are saturated and unreactive with the oxidants. They do not react sufficiently to produce the biocide of the present invention Oxidants are reacted with the amine source to produce the biocides useful in the present invention. The oxidants used in the present invention include, but are not limited to, chlorine, hypochlorite, hypochlorous acid, chlorine dioxide, chlorinated isocyanurates, bromine, hypobromite, hypobromous acid, bromine chloride, electrolytically-generated chlorites, electrolytically-generated bromites, halogenated hydantoins, ozone, and peroxy compounds such as perborate, percarbonate persulfate, hydrogen peroxide, percarboxylic acid, and peracetic acid.

In one particular advantageous embodiment of the invention, the ammonium and/or amine source is ammonium hydroxide and the oxidant is sodium hypochlorite.

In another particular advantageous embodiment of the invention, the ammonium and/or amine source is ammonium sulfate and the oxidant is sodium hypochlorite.

The biocidal mixtures or methods of this invention are effective for controlling and inhibiting the growth and reproduction of microorganisms in aqueous systems and additive aqueous systems. Aqueous systems include industrial waters systems such as cooling water systems, pulp and paper systems, petroleum operations, industrial lubricants and coolants, lagoons, lakes and ponds. Aqueous systems include additive aqueous systems. In addition, the aqueous systems in which the present invention can be used include, but are not limited to, those involved in, paints, leather, wood, wood pulp, wood chips, starch, clays, retention aids, sizing agents, defoamers, dry and wet strength additives, pigment slurries (e.g., precipitated calcium carbonate), proteinaceous materials, lumber, animal hides, vegetable tanning liquors, cosmetics, toiletry formulations, emulsions, adhesives, coatings, metalworking fluids, swimming pool water, textiles, heat exchangers, pharmaceutical formulations, geological drilling lubricants, and agrochemical compositions.

An additive aqueous system is an aqueous system that is or will be added into a larger aqueous system. Such aqueous additive systems in the pulp and paper industry include, but are not limited to, retention aids, sizing agents, defoamers, dry and wet strength additives and pigment slurries.

The dosage amounts of the monohaloamine and dihaloamine required for effectiveness in this invention generally depend on the nature of the aqueous system being treated, the level of organisms present in the aqueous system, and the level of inhibition desired. A person skilled in the art, using the information disclosed herein could determine the amount necessary without undue experimentation.

Effective concentrations of monohaloamine, such as monochloramine, on an active level basis, are from about 0.01 milligram per liter (mg/l) to about 1000 mg/l by weight, (i.e., based on the weight of monohaloamine as measured by the amount of available chlorine [in mg/l]) and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. The amount of dihaloamine, on an active level basis, is from about 0.01 parts per million (mg/l) to about 1000 mg/l by weight (i.e., based on the weight of dihaloamine as measured by the amount of available chlorine [in mg/l]), and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. Thus, with respect to the biocides, the lower and upper limits of the required concentrations substantially depend upon the system to be treated.

The ratio of monohaloamine to dihaloamine is from about 200:1 to about 1:100, preferably from about 30:1 to 1:5, more preferably from 20:1 to about 1:5 or 20:1 to 1:4.

In one embodiment of the invention monohaloamine is added to the aqueous system before dihaloamine. In another embodiment of the invention dihaloamine is added before the monohaloamine. In yet another embodiment of the invention, monohaloamine and dihaloamine are added simultaneously to the system to be treated.

In another embodiment, after the addition of monohaloamine, dihaloamine is added to the aqueous system. The time lag between the addition of monohaloamine and dihaloamine can be, but is not limited to, up to 30 minutes, or up to 15 minutes, or up to 5 minutes, or up to 1 minute.

In another embodiment, after the addition of dihaloamine, monohaloamine is added to the aqueous system. The time lag between the addition of dihaloamine and monohaloamine can be, but is not limited to, up to 30 minutes, or up to 15 minutes, or up to 5 minutes, or up to 1 minute.

In yet another embodiment, monohaloamine and dihaloamine are added to the aqueous system simultaneously.

In yet another embodiment the mixed haloamine blend can be produced in situ by addition of ammonium or amine source and halogenated oxidizer to the process water to cause formation of the monochloramine after which a measurable amount of acid is added to the water to lower the pH to a point sufficient to cause formation of dichloramine.

In any embodiment, monohaloamine can be added pursuant to any known method that provides the desired concentration of monohaloamine in the aqueous system. Similar to monohaloamine, in any embodiment, dihaloamine can be added pursuant to any known method that provides the desired concentration of dihaloamine in the aqueous system. Either or both monohaloamine and dihaloamine can be feed continuously, intermittently, or alternately to aqueous systems.

The haloamines can be added to the system as independent material(s) or in combination with other materials being added to the aqueous system being treated system. For example, a synergistic combination of monohaloamine and dihaloamine can be added with starch, clay, pigment slurries, precipitated calcium carbonate, retention aids, sizing aids, dry and/or wet strength additives, defoamers or other additives used in the manufacturing of pulp or paper products.

The haloamines can be continuously, intermittently, or alternately added to aqueous and/or additive systems. The above feed strategies for biocide addition are dependent on the growth of the microbial population, the type of problematic microorganisms and the degree of surface fouling in a particular system. A monohaloamine and dihaloamine blend can be used in the treatment of additive systems, (i.e., starch makedown solutions, retention aid makedown solutions, precipitated calcium carbonate slurries, etc.) or other feed points within the aqueous system (i.e., short or long loop, broke chest, saveall, thick stock, blend chest, head box).

The present invention will now be described with reference to specific examples which are to be regarded as solely illustrative and not as restricting the scope of the present invention.

EXAMPLES

All raw materials used in the following examples were research grade reagents obtained from Sigma-Aldrich (St. Louis, Mo., USA) unless noted otherwise Preparation of the Monochloramine (MCA) Stock Solution A dilute sodium hypochlorite solution was prepared by diluting 1.122 ml concentrated aqueous sodium hypochlorite (11.7% by weight) in 78.878 ml of tap water. Separately a dilute solution of ammonium sulfate was prepared by diluting a 0.304 ml of a concentrated aqueous solution of ammonium sulfate (40% by weight) in 19.696 ml of tap water. The dilute sodium hypochlorite solution was then added to the diluted ammonium sulfate solution with stirring yield a solution with pH of 8.92. The solution was analyzed spectrophotometrically by measuring the absorbance of light in the range of 250-350 nm and found to be MCA (absorbance peak at 244 nm). The concentration of the MCA solution was adjusted to 1,250 ppm actives as $Cl_2$ as determined by the Hach DPD chlorine test (Hach Company, Loveland, Colo., USA).

Preparation of the Dichloramine (DCA) Stock Solution

A dilute sodium hypochlorite solution was prepared by diluting 4.487 ml concentrated aqueous sodium hypochlorite (11.7% by weight) in 75.511 ml of tap water. Separately a dilute solution of ammonium sulfate was prepared by diluting a 1.216 ml of a concentrated aqueous solution of ammonium sulfate (40% by weight) in 18.784 ml of tap water. The dilute sodium hypochlorite solution was then added to the dilute ammonium sulfate solution with stirring yield a solution with pH of 8.98. Dilute sulfuric acid (5 wt %) was then added dropwise with mixing to lower the pH to approximately 5.0. The solution was analyzed spectrophotometrically by measuring the absorbance of light in the range of 250-350 nm and found to be DCA (absorbance peak at 295 nm). The concentration of the DCA solution was adjusted to measured to be 4,700 ppm actives as $Cl_2$ as determined by the Hach DPD chlorine test.

Preparation of the M9 Minimal Salt Media

Sodium phosphate dibasic heptahydrate (64.0 g), potassium phosphate monobasic (15.0 g), sodium chloride (2.5 g) and ammonium chloride (5.0 g) were dissolved in deionized water to yield a volume of 1 L. The 1 L solution was separated into 200 ml aliquots and sterilized by autoclave. A 200 ml sterilized aliquot was then added with mixing to sterilized deionized water along with sterilized aqueous solutions of 2.0 ml magnesium sulfate (1M), 0.1 ml calcium chloride (1M), 20.0 ml glucose (20% by weight), and 1.0 ml yeast extract (BD-Diagnostic Systems, Sparks, Md., USA) (10% by weight) to yield a volume of 1 L. After all components were observed to dissolve visually, mixing was discontinued, and the solution was filtered through a 0.22 micron filter to yield the M9 minimal salt media.

Synergy Testing

Synergy testing of MCA and DCA was performed following the teaching and definitions reported in Kull et al., *Letters in Applied Microbiology*, Vol. 9, pgs. 538-541, 1961. The method measures the minimal inhibitory concentration (MIC) two biocides by themselves, and also of multiple binary combinations of the two biocides.

The M9 minimal salt media was adjusted to the desired test pH with either dilute aqueous hydrochloric or sodium hydroxide. The wells in Column 1 of a 144 well microtitre plate configuration (12 columns×12 rows) were then filled with 252 μl of pH adjusted M9 media, and the remaining wells of Columns 2-12 were filled with 140 μl of pH adjusted M9 media. 28 μl of the 1,250 ppm MCA stock was then added to each well of Column 1. After mixing, 140 μl of the mixture from the wells in Column 1 was removed and serially diluted two-fold across the plate to Column 11. 140 μl of solution was then removed from the wells in Column 11 such that each well in the series comprised of 140 μl of pH adjusted M9 and some level of MCA. Column 12 was left a biocide-free control.

The DCA dilutions were conducted in a similar fashion on a separate 144 well microtitre plate configuration. Each well of Row 1 was filled with 131 μl of the pH adjusted M9 media, while the remaining wells Rows 2-12 were filled with 140 μl of the pH adjusted M9 media. Then, 149 μl of the 4,700 ppm DCA stock solution was added to each well of Row 1 and mixed. A series of two-fold dilutions was then made down the plate to Row 11. 140 μl of solution was then removed from the wells in Row 11 such that each well in the series comprised of 140 μl of pH adjusted M9 and some level of DCA. Row 12 was left a biocide-free control.

7 μl from each well of the DCA stock plate was transferred to the corresponding well of the MCA stock plate to yield a synergy plate comprising different combinations of MCA and DCA. Each well of the synergy plate was then inoculated with 5 μl of an approximately $10^8$ cfu/ml culture of $P.$ $aeruginosa$ (ATCC 10145) that was diluted 1:100. The plate was then sealed and then incubated overnight at 28° C. After 20-24 hours, the plate was scored by determining the first well of a dilution series to show no growth.

The synergy index (SI) was then calculated for any combination showing an endpoint (eg., no growth) using the formula Qa/QA+Qb/QB=synergy index (SI). In this formula QA represents the MIC of biocide A by itself, and Qa is the concentration of biocide A in the combination which produces the endpoint. QB is the MIC of the biocide B by itself, and Qb is the concentration of biocide B in the combination producing the endpoint. A synergy index of 1.0 indicates no interaction of the two biocides other then an additive effect, an SI of less then 1.0 indicates a synergistic interaction, and an SI of greater then 1.0 indicates an antagonistic relationship between the two biocides.

The MIC values in ppm of MCA and DCA alone, and in combination with each other, are summarize in Table I. In each case the values represent the concentrations in combination which produces the endpoint of no growth, visualized as the first well in the dilution series which has no visible growth. The values presented are the average of multiple independent determinations.

TABLE I

| Example | pH | MCA ppm[1] (QA) | DCA ppm[1] (QB) | MCA ppm[1] (Qa) | DCA ppm[1] (Qb) | MCA:DCA Ratio | Synergy Index |
|---|---|---|---|---|---|---|---|
| 1 | 5 | 2.5 | 0.33 | 0.05 | 0.2 | 0.25 | 0.63 |
| 2 | 5 | 2.5 | 0.33 | 0.2 | 0.2 | 1 | 0.69 |
| 3 | 5 | 2.5 | 0.33 | 0.4 | 0.1 | 4 | 0.46 |
| 4 | 5 | 2.5 | 0.33 | 0.8 | 0.1 | 8 | 0.62 |
| 5 | 5 | 2.5 | 0.33 | 0.8 | 0.05 | 16 | 0.47 |
| 6 | 5 | 2.5 | 0.33 | 0.8 | 0.025 | 32 | 0.40 |
| 7 | 5 | 2.5 | 0.33 | 0.8 | 0.013 | 62 | 0.36 |
| 8 | 5 | 2.5 | 0.33 | 1.5 | 0.013 | 115 | 0.64 |
| 9 | 5 | 2.5 | 0.33 | 2.5 | 0 | NA | NA |
| 10 | 5 | 2.5 | 0.33 | 0 | 0.33 | NA | NA |
| 11 | 8 | 2.6 | 0.38 | 0.05 | 0.2 | 0.25 | 0.55 |
| 12 | 8 | 2.6 | 0.38 | 0.2 | 0.2 | 1 | 0.60 |
| 13 | 8 | 2.6 | 0.38 | 0.8 | 0.1 | 8 | 0.57 |
| 14 | 8 | 2.6 | 0.38 | 1.5 | 0.1 | 15 | 0.84 |
| 15 | 8 | 2.6 | 0.38 | 0.8 | 0.05 | 16 | 0.44 |
| 16 | 8 | 2.6 | 0.38 | 1.5 | 0.025 | 60 | 0.64 |
| 17 | 8 | 2.6 | 0.38 | 1.5 | 0.013 | 115 | 0.61 |
| 18 | 8 | 2.6 | 0.38 | 2.6 | 0 | NA | NA |
| 19 | 8 | 2.6 | 0.38 | 0 | 0.38 | NA | NA |
| 20 | 9 | 1.5 | 0.33 | 0.4 | 0.2 | 2 | 0.87 |
| 21 | 9 | 1.5 | 0.33 | 0.8 | 0.1 | 8 | 0.84 |
| 22 | 9 | 1.5 | 0.33 | 0.8 | 0.05 | 16 | 0.68 |
| 23 | 9 | 1.5 | 0.33 | 1.5 | 0 | NA | NA |
| 24 | 9 | 1.5 | 0.33 | 0 | 0.33 | NA | NA |

[1]As ppm of $Cl_2$ per characterization by the Hach DPD chlorine test.

These results indicate MCA and DCA are synergistic at pH 5, 8 and 9, and that the synergism exists at a range of ratios of MCA:DCA, respectively.

The invention claimed is:

1. A method for controlling the growth of bacteria in an aqueous systems, comprises forming a blend of monochloramine and dichloramine with a ratio of monochloramine to dichloramine of from 30:1 to 1:5 and subsequently adding an effective amount of said blend to the aqueous system, wherein said aqueous system is a pulp and paper mill water system and has a pH in the range of from 5 to 9.

2. The method of claim 1, wherein the ratio of monochloramine to dichloramine is from 20:1 to 1:5 and subsequently adding an effective amount of said blend to the aqueous system, wherein said aqueous system is a pulp and paper mill water system and has a pH in the range of from 5 to 9.

3. The method of claim 1, wherein the monochloramine is produced by contacting an ammonium or an amine source with a chlorinated oxidant or in the alternative by contacting the ammonium or amine source with an oxidizer in the presence of a chlorine source.

4. The method of claim 3, wherein the amine source is selected from the group consisting of polyamines, primary amines, secondary amines, cyclic amines, aliphatic amines, aromatic amines, primary and secondary nitrogen containing polymers and combinations thereof.

5. The method of claim 4, wherein the amine source is selected from the group consisting of dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallowmethylamine, coco-methylamine, n-alkylamines, n-acetylglucosamine, diphenylamine, ethanol/methylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, and combinations thereof.

6. The method of claim 3, wherein the chlorinated oxidant is selected from the group consisting of chlorine, hypochlorite, hypochlorous acid, chlorinated isocyanurates, chlorinated hydantoins, and combinations thereof.

7. The method of claim 3, wherein the oxidant is selected from ozone, a peroxy compound or combinations thereof.

8. The method of claim 3, wherein the chlorinated oxidant comprises hypochlorous acid or hypochlorite.

9. The method of claim 1, wherein the dichloramine is produced by reacting an ammonium or an amine source with a chlorinated oxidant.

10. The method of claim 1, wherein the dichloramine is produced by decreasing the pH of a monochloramine-containing solution.

11. The method of claim 1, wherein the dichloramine is produced by changing the proportion of halogen to nitrogen in a monochloramine-containing solution.

12. The method of claim 1, wherein the monochloramine is produced from an amine or ammonium source comprising ammonia or ammonium hydroxide.

13. The method of claim 1, wherein monochloramine is produced from an amine or ammonium source comprising an ammonium salt.

14. The method of claim 13, wherein the ammonium salt is selected from the group consisting of ammonium sulfate, ammonium acetate, ammonium bicarbonate, ammonium carbonate, ammonium chloride, ammonium citrate, ammonium iodide, ammonium molybdate, ammonium nitrate, ammonium oxalate, ammonium persulfate, ammonium phosphate, ammonium sulfate, ammonium sulfide, ammonium sulfamate and combinations thereof.

15. The method of claim 1, wherein the amount of ratio of monochloramine, on an active level basis, ranges from about 0.01 to about 1000 mg/L as $Cl_2$ based on the volume of the aqueous system being treated.

16. The method of claim 1, wherein the amount of ratio of monochloramine ranges from about 0.05 to about 200 mg/L as $Cl_2$ on an active level basis.

17. The method of claim 1, wherein the blend is continuously, intermittently, or alternately added to the aqueous system.

18. The method of claim 1, wherein the amount of ratio of dichloramine, on an active level basis, ranges from about 0.01 to about 1000 mg/L as $Cl_2$ based on the volume of the aqueous system being treated.

19. The method of claim 1, wherein the amount of ratio of dichloramine ranges from about 0.05 to about 200 mg/L as $Cl_2$ on an active level basis.

* * * * *